(12) United States Patent
Elokdah et al.

(10) Patent No.: US 6,448,255 B1
(45) Date of Patent: Sep. 10, 2002

(54) IMIDAZO-ISOQUINOLIN-5-ONE DERIVATIVES, PYRIMIDO-ISOQUINOLIN-6-ONE DERIVATIVES AND IMIDAZO-NAPHTHYRIDIN-5-ONE DERIVATIVES

(75) Inventors: Hassan M. Elokdah, Yardley; Theodore S. Sulkowski, Wayne, both of PA (US); Sie-Yearl Chai, Lawrenceville; John Babiak, Martinsville, both of NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/965,957

(22) Filed: Sep. 28, 2001

Related U.S. Application Data

(60) Provisional application No. 60/237,304, filed on Oct. 2, 2000.

(51) Int. Cl.⁷ .................. C07D 487/04; C07D 487/14; A61K 31/4745; A61K 31/519
(52) U.S. Cl. ............... 514/267; 514/285; 514/292; 514/293; 544/252; 546/70; 546/82; 546/84
(58) Field of Search ............... 544/252; 546/70, 546/82, 84; 514/267, 285, 292, 293

(56) References Cited

PUBLICATIONS

Elokdah et al., Design and Synthesis of Tricyclic Derivatives as High Density Lipoprotein Cholesterol Enhancers, Biorganic & Medicinal Chemistry Letters, 11(3), pp. 339–342, Feb. 2001.*
Johnson, Chemical Abstract 84:105492, 1976.*
Gofman et al, Circulation, 34, 1966, 679–697.
Miller and Miller, Lancet, 1, 1975, 16–19.
Gordon et al, Circulation, 79, 1989, 8–15.
Stampfer et al, N. Engl. J. Med., 325, 1991, 373–381.
Badimon et al, Lab. Invest., 60, 1989, 455–461.
Miller et al, Br. Med. J., 282, 1981, 1741–1744.
Picardo et al, Arteriosclerosis, 6, 1986, 434–441.
Glomset, J. Lipid Res., 9, 1968, 155–167.
Glass et al, J. Biol. Chem., 258, 1983, 7161–7167.
MacKinnon et al, J. Biol. Chem., 261, 1986, 2548–2552.
Grow and Fried, J. Biol. Chem., 253, 1978, 1834–1841.
Lagocki and Scanu, J. Biol. Chem., 255, 1980, 3701–3706.
Schaefer et al, J. Lipid Res., 23, 1982, 1259–1273.

* cited by examiner

Primary Examiner—Deepak R. Rao
(74) Attorney, Agent, or Firm—Michael R. Nagy

(57) ABSTRACT

Antiatherosclerotic compounds are provided which have the following structure:

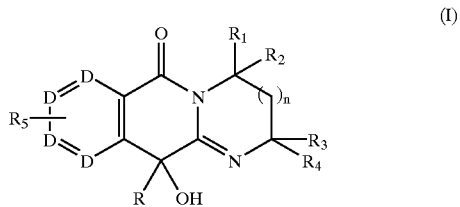

(I)

wherein:
R is hydrogen, lower alkyl, alkenyl, alkynyl, aryl, heteroaryl, or aryl or heteroaryl substituted with one or more members of the group consisting of alkyl, hydroxy, alkoxy, perfluoroalkyl, perfluoroalkoxy, alkylthio, nitro, amino, mono or di-alkylamino, and halogen;
D is C—H, carbon bound to $R_5$ or nitrogen;
$R_1$, $R_2$, $R_3$, and $R_4$ are each independently hydrogen, alkyl, or taken together form a ring;
$R_5$ is one or more groups selected from hydrogen, alkyl, alkenyl, alkynyl, aryl, hydroxy, alkoxy, perfluoroalkyl, perfluoroalkoxy, alkylthio, nitro, amino, mono or di-alkylamino, or halogen;
n is an integer of 0–3;
or pharmaceutically acceptable salts thereof.

11 Claims, No Drawings

IMIDAZO-ISOQUINOLIN-5-ONE DERIVATIVES, PYRIMIDO-ISOQUINOLIN-6-ONE DERIVATIVES AND IMIDAZO-NAPHTHYRIDIN-5-ONE DERIVATIVES

This application claims priority from provisional application Ser. No. 60/237,304, filed Oct. 2, 2000, the entire disclosure of which is hereby incorporated by reference.

FIELD OF THE INVENTION

The present invention is directed to anti-atherosclerotic agents and more specifically, to compounds, compositions and methods for treating atherosclerotic conditions, such as dyslipoproteinemias and coronary heart disease. This invention specifically relates to compounds which elevate HDL cholesterol concentration and which may be useful for the treatment of atherosclerotic conditions and coronary heart disease.

BACKGROUND OF THE INVENTION

Numerous studies have demonstrated that both the risk of coronary heart disease (CHD) in humans and the severity of experimental atherosclerosis in animals are inversely correlated with serum HDL cholesterol (HDL-C) concentrations (Ross et al, *Am. J. Med.*, 11 (1951) 480–493; Gofman et al, *Circulation*, 34 (1966) 679–697; Miller and Miller, *Lancet*, 1 (1975) 16–19; Gordon et al, *Circulation*, 79 (1989) 8–15; Stampfer et al, *N. Engl. J. Med.*, 325 (1991) 373–381; Badimon et al, *Lab. Invest.*, 60 (1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated level of some HDL particles in humans appears to be correlated to a decreased number of sites of stenosis in the coronary arteries of humans (Miller et al, *Br. Med. J.*, 282 (1981) 1741–1744).

There are several mechanisms by which HDL may protect against the progression of atherosclerosis. Studies in vitro have shown that HDL is capable of removing cholesterol from cells (Picardo et al, *Arteriosclerosis*, 6 (1986) 434–441). Data of this nature suggest that one antiatherogenic property of HDL may lie in its ability to deplete tissues of excess free cholesterol and eventually lead to the delivery of this cholesterol to the liver (Glomset, *J. Lipid Res.*, 9 (1968) 155–167). This has been supported by experiments showing efficient transfer of cholesterol from HDL to the liver (Glass et al, *J. Biol. Chem.*, 258 (1983) 7161–7167; MacKinnon et al, *J. Biol. Chem.*, 261 (1986) 2548–2552). In addition, HDL may serve as a reservoir in the circulation for apoproteins necessary for the rapid metabolism of triglyceride-rich lipoproteins (Grow and Fried, *J. Biol. Chem.*, 253 (1978) 1834–1841; Lagocki and Scanu, *J. Biol. Chem.*, 255 (1980) 3701–3706; Schaefer et al, *J. Lipid Res.*, 23 (1982) 1259–1273). Accordingly, agents which increase HDL cholesterol concentrations are useful as anti-atherosclerotic agents, particularly in the treatment of dyslipoproteinemias and coronary heart disease.

SUMMARY OF THE INVENTION

In accordance with this invention there is provided compounds of formula I:

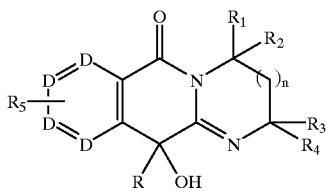

(I)

wherein:
R is hydrogen, lower alkyl, alkenyl, alkynyl, aryl, heteroaryl, or aryl or heteroaryl substituted with one or more members of the group consisting of alkyl, hydroxy, alkoxy, perfluoroalkyl, perfluoroalkoxy, alkylthio, nitro, amino, mono- or di-alkylamino, and halogen;
D is C—H, carbon bound to $R_5$ or nitrogen;
$R_1$, $R_2$, $R_3$, and $R_4$ are each independently hydrogen, alkyl, or taken together form a ring;
$R_5$ is one or more groups selected from hydrogen, alkyl, alkenyl, alkynyl, aryl, hydroxy, alkoxy, perfluoroalkyl, perfluoroalkoxy, alkylthio, nitro, amino, mono- or di-alkylamino, or halogen;
n is an integer of 0–3;
or pharmaceutically acceptable salts thereof.

The present invention is further directed to a method of treating atherosclerosis in a mammal in need thereof which comprises administering to the mammal an anti-atherosclerotic effective amount of compound of Formula I:

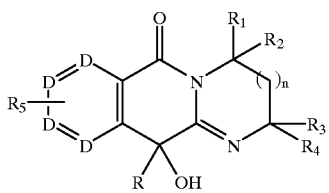

(I)

wherein:
R is hydrogen, lower alkyl, alkenyl, alkynyl, aryl, heteroaryl, or aryl or heteroaryl substituted with one or more members of the group consisting of alkyl, hydroxy, alkoxy, perfluoroalkyl, perfluoroalkoxy, alkylthio, nitro, amino, mono or di-alkylamino, and halogen;
D is C—H, carbon bound to $R_5$ or nitrogen;
$R_1$, $R_2$, $R_3$, and $R_4$ are independently hydrogen, alkyl, or taken together form a ring.
$R_5$ is one or more groups optionally selected from hydrogen, alkyl, alkenyl, alkynyl, aryl, hydroxy, alkoxy, perfluoroalkyl, perfluoroalkoxy, alkylthio, nitro, amino, mono or di-alkylamino, or halogen;
n is an integer of 0–3;
or pharmaceutically acceptable salts thereof.

DETAILED DESCRIPTION OF THE INVENTION

Preferably, the present invention is directed to compounds of Formula I, wherein R is aryl; D is C—H; $R_1$, $R_2$, $R_3$, and $R_4$ are each independently hydrogen, alkyl, or taken together form a ring; $R_5$ is halogen; n is 0–1; or pharmaceutically acceptable salts thereof.

As used herein, the term "lower alkyl" refers to both straight and branched chain moieties of 1–6 carbon atoms. The term "aryl" includes aromatic radicals of 6–12 carbon atoms. The term "halogen" includes fluorine, chlorine, bromine, and iodine.

The pharmaceutically acceptable salts of the present compounds include those derived from organic and inorganic acids such as, but not limited to: acetic, lactic, citric, tartaric, succinic, fumaric, maleic, malonic, mandelic, malic, hydrochloric, hydrobromic, phosphoric, nitric, sulfuric, methanesulfonic, toluene sulfonic, and similarly known, acceptable acids.

The most preferred compounds of this invention are:
10-Hydroxy-2,2-dimethyl-10-phenyl-2,10-dihydroimidazo [1,2-b]isoquinolin-5(3H)-one;
11-(4-Fluorophenyl)-11-hydroxy-2,3,4,11-tetrahydro-6H-pyrimido[1,2-b]isoquinolin-6-one;
10-(4-Fluorophenyl)-10-hydroxy-2,2-dimethyl-2,10-dihydroimidazo[1,2-b]isoquinolin-5(3H)-one;
6-(4-Fluorophenyl)-6-hydroxy-1,3,4,4a,6,12a-hexahydrobenzimidazo[1,2-b]isoquinolin-11 (2H)-one;
(2R,10S)-10-(4-Fluorophenyl)-10-hydroxy-2-methyl-2,10-dihydroimidazo[1,2-b]isoquinolin-5(3H)-one;
(2S, 10S)-10-(4-Fluorophenyl)-10-hydroxy-2-methyl-2,10-dihydroimidazo[1,2-b]isoquinolin-5(3H)-one; and
10-(4-Chlorophenyl)-10-hydroxy-2,2-dimethyl-2,10-dihydroimidazo[2,1-g][1,7]naphthyridin-5(3H)-one.

The compounds of the present invention can be readily prepared according to the following reaction scheme or modification thereof using readily available starting materials, reagents and conventional synthetic procedures. It is also possible to make use of variants of these process steps, which in themselves are known to and well within the preparatory skill of the medicinal chemist. In the following reaction schemes, R is a group selected from hydrogen, lower alkyl, alkenyl, alkynyl, aryl, heteroaryl, aryl/heteroaryl optionally substituted with one or more groups selected from alkyl of 1–6 carbon atom, hydroxy, alkoxy, perfluoroalkyl, perfluoroalkoxy, alkylthio, nitro, amino, mono or di-alkylamino, or halogen; D is C—H, Carbon bound to $R_5$ or Nitrogen; $R_1$, $R_2$, $R_3$, and $R_4$ are independently hydrogen, lower alkyl, or taken together as a ring; $R_5$ is one or more groups optionally selected from hydrogen, lower alkyl, alkenyl, alkynyl, aryl, hydroxy, alkoxy, perfluoroalkyl, perfluoroalkoxy, alkylthio, nitro, amino, mono or di-alkylamino, or halogen, and n is an integer of 0–3.

Preparation of 3-carboxamido phthalides (VII) from o-acyl benzoic acids (II) in a 5-step process has been described in the literature (Hauser, C. R., Tetenbaum, M. T. and Hoffenberg, D. S.; *J. Org. Chem.,* 23, 861 (1958)). The procedure, as outlined in scheme I, involves reduction of the o-acyl benzoic acid (II) to the lactone (III). Metalation of the 3-position of III and subsequent quenching with carbon dioxide afforded the lactone acid (V). Conversion of V to the corresponding acid chloride (VI) followed by treatment with ammonia afforded the 3-carboxamido phthalides (VII).

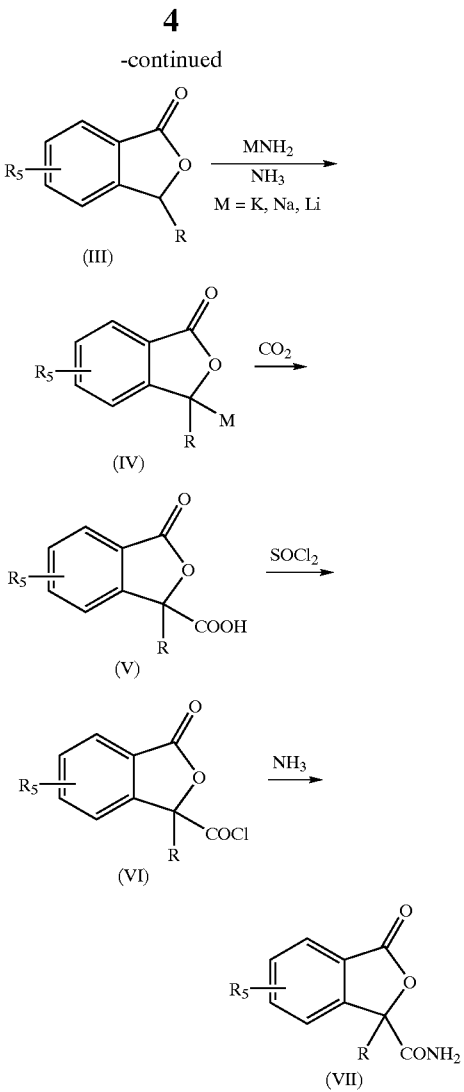

In the present invention, o-acyl benzoic acids (II) are converted to the corresponding 3-carboxamido phthalides (VII) in a one step process. The process is novel and widely applicable. Reaction of o-acyl benzoic acids with potassium cyanide (Scheme II) was carried out in acetic acid by heating in a steam bath for 17 to 70 hours either in a round bottom flask or in a stoppered pressure bottle to yield 3-carboxamido phthalides (VII). Reaction of VII with diamines in toluene was carried out by refluxing for 18 to 72 hours in a flask equipped with a water separator affording the tricyclic derivatives (I).

Scheme I

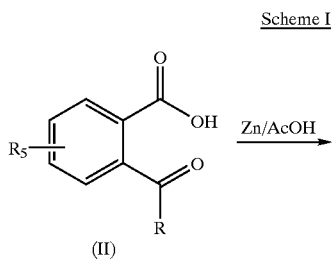

Scheme II

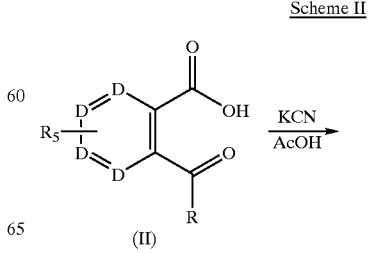

-continued

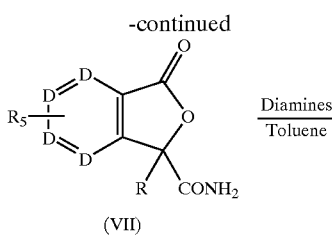

(VII)

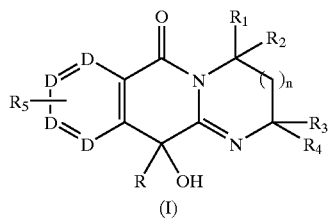

(I)

This invention also provides pharmaceutical compositions comprised of tricyclic derivatives (I) either alone or in combination with excipients (i.e. pharmaceutically acceptable materials with no pharmacological effects). Such compositions are useful in the treatment of atherosclerotic conditions such as dyslipoproteinemias and coronary heart disease, in that they increase the blood serum high density lipoprotein concentration of mammals treated with the compounds.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid, which is in admixture with the finely divided active ingredient. In tablets, the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physician's direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of HDL and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The ability of the compounds of this invention to increase blood serum HDL levels was established by the following standard experimental procedure for determination of HDL cholesterol:

Male Sprague-Dawley rats weighing 200–225 g were housed two per cage and fed Purina Rodent Chow Special Mix 5001-S supplemented with 0.25% cholic acid and 1.0% cholesterol and water ad libitum for 8 days. Each test substance was administered to a group of six rats fed the same diet with the test diet mixed in as 0.005–0.1% of the total diet. Body weight and food consumption were recorded prior to diet administration and at termination. Typical doses of the test substances were 5–100 mg/kg/day.

At termination, blood was collected from anesthetized rats and the serum was separated by centrifugation. Total serum cholesterol was assayed using the Sigma Diagnostics enzymatic kit for the determination of cholesterol, Procedure No. 352, modified for use with ninety-six well microtiter plates. After reconstitution with water the reagent contains 300 U/l cholesterol oxidase, 100 U/l cholesterol esterase, 1000 U/l horse radish peroxidase, 0.3 mmoles/l 4-aminoantipyrine and 30.0 mmoles/l p-hydroxybenzenesulfonate in a pH 6.5 buffer. In the reaction cholesterol was oxidized to produce hydrogen peroxide which was used to form a quinoneimine dye. The concentration of dye formed was measured spectrophotometrically by absorbency at 490 nm after incubation at 25° C. for 30 minutes. The concentration of cholesterol was determined for each serum sample relative to a commercial standard from Sigma.

HDL cholesterol concentrations in serum were determined by separation of lipoprotein classes by fast protein liquid chromatography (FPLC) by a modification of the method of Kieft et al., *J. Lipid Res.*, 32 (1991) 859–866. 25 ul of serum was injected onto Superose 12 and Superose 6 (Pharmacia), in series, with a column buffer of 0.05 M Tris (2-amino-2-hydroxymethyl-1,3-propanediol) and 0.15 M sodium chloride at a flow rate of 0.5 ml/min. The eluted sample was mixed on line with Boehringer-Mannheim cholesterol reagent pumped at 0.2 m/min. The combined eluents were mixed and incubated on line through a knitted coil (Applied Biosciences) maintained at a temperature of 45 C. The eluent was monitored by measuring absorbence at 490 nm and gave a continuous absorbence signal proportional to the cholesterol concentration. The relative concentration of each lipoprotein class was calculated as the percent of total absorbence. HDL cholesterol concentration, in serum, was calculated as the percent of total cholesterol as determined by FPLC multiplied by the total serum cholesterol concentration.

The compounds of the present invention increase HDL cholesterol concentrations as summarized in Table I:

TABLE I

| Compound of Example | Dose (mg/kg/day) | HDL Cholesterol Level Increase (%) |
|---|---|---|
| 1. | 100 | 55 |
| 2. | 100 | 22 |
| 3. | 100 | 90 |
| 4. | 100 | 21 |
| 5. | 100 | 105 |
| 6. | 100 | 38 |
| 7. | 100 | 49 |

The following non-limiting examples illustrate the preparation of representative compounds of the invention:

EXAMPLE 1

Step 1

3-Oxo-1-phenyl-1,3-dihydro-2-benzofuran-1-carboxamide

A mixture of 2-benzoylbenzoic acid (75 g), potassium cyanide (35 g), and glacial acetic acid (175 mL) was heated at 115–125° C. in a sealed pressure bottle for 70 h. After cooling to ambient temperature, the precipitated solid was collected by filtration, washed with water and ethanol then crystallized from ethanol to give the title compound (45 g), m. p. 225–227° C.

Anal. for $C_{15}H_{11}NO_3$: Calculated: C, 71.14; H, 4.38; N, 5.53. Found: C, 71.32; H, 4.36; N, 5.54.

Step 2

10-Hydroxy-2,2-dimethyl-10-phenyl-2,10-dihydroimidazo[1,2-b]isoquinolin-5(3H)-one A mixture of 3-oxo-1-phenyl-1,3-dihydro-2-benzofuran-1-carboxamide (10 g), 2-methyl-1,2-diaminopropane (15 mL), and toluene (100 mL) was heated at reflux for 18 h in a flask equipped with a water separator. The mixture was cooled to ambient temperature and extracted with water. The organic phase was dried over anhydrous magnesium sulfate and evaporated to dryness. The residue was crystallized from ethanol to give the title compound (57.3 g), m.p. 186–188° C.

Anal. for $C_{19}H_{18}N_2O_2$: Calculated: C, 74.49; H, 5.92; N, 9.14. Found: C, 74.74; H, 5.92; N, 9.07.

EXAMPLE 2

Step 1

1-(4-Fluorophenyl)-3-oxo-1,3-dihydro-2-benzofuran-1-carboxamide

A mixture of 2-(4-fluorobenzoyl)benzoic acid (75 g), potassium cyanide (28 g), and glacial acetic acid (160 mL) was heated at 115–125 C. in a sealed pressure bottle for 48 h. After cooling to ambient temperature, the mixture was poured into ice water (1.5L). The solid was collected by filtration and crystallized from ethanol to give the title compound (42 g) as a white solid, m. p. 170–173° C. Mass spectrum (EI, M+) m/z 271.

Anal. for $C_{15}H_{10}NO_3F$: Calculated C, 66.42; H, 3.72; N, 5.16. Found: C, 66.06; H, 3.83; N, 5.14.

Step 2

11-(4-Fluorophenyl)-11-hydroxy-2,3,4,11-tetrahydro-6H-pyrimido[1,2-b]isoquinolin-6-one A mixture of 1-(4-fluorophenyl)-3-oxo-1,3-dihydro-2-benzofuran-1-carboxamide (17 g), 1,3-diaminopropane (25 mL), and toluene (125 mL) was heated at reflux for 19 h in a flask equipped with a water separator. The mixture was cooled to ambient temperature and extracted with water, and evaporated to dryness. The residue was crystallized from ethanol to give the title compound (26 g) as a solid, m.p. 126–128° C.

Anal. for $C_{18}H_{15}N_2O_2F$: Calculated C, 69.67; H, 4.87; N, 9.03. Found: C, 69.93; H, 4.98; N, 8.98.

EXAMPLE 3

10-(4-Fluorophenyl)-10-hydroxy-2,2-dimethyl-2,10-dihydroimidazo[1,2-b]isoquinolin-5(3H)-one A mixture of 1-(4-fluorophenyl)-3-oxo-1,3-dihydro-2-benzofuran-1-carboxamide (25 g) (Step 1 of Example 2), 2-methyl-1,2-diaminopropane (40 mL), and toluene (125 mL) was heated at reflux for 18 h in a flask equipped with a water separator. The mixture was cooled to ambient temperature and extracted with water. The organic phase was dried over anhydrous magnesium sulfate and evaporated to dryness. The residue was slurried with ethanol. The solid was collected by filtration and dried to give the title compound (26 g) as a white solid, m.p. 168–170° C. Anal. for $C_{19}H_{17}N_2O_2F$: Calculated: C, 70.35; H, 5.28; N, 8.64. Found: C, 70.16; H, 5.35; N, 8.55.

EXAMPLE 4

6-(4-Fluorophenyl)-6-hydroxy-1,3,4,4a,6,12a-hexahydrobenzimidazo[1,2-b]isoquinolin-11(2H)-one A mixture of 1-(4-fluorophenyl)-3-oxo-1,3-dihydro-2-benzofuran-1-carboxamide (5 g) (Step 1 of Example 2), trans 1,2-diaminocyclohexane (8.3 g), and toluene (75 mL) was heated at reflux for 66 h in a flask equipped with a water separator. The mixture was evaporated to dryness and the residual gum was extracted with hexane. The residue was chromatographed over silica gel and eluted with 10% methanol in methylene. Crystallization from ethyl acetate afforded the title compound (2.7 g) as a white solid m.p. 203–205° C.

9

Anal. for $C_{21}H_{19}N_2O_2F$: Calculated C, 71.99; H, 5.47; N, 8.00. Found: C, 71.85; H, 5.54; N, 7.95.

EXAMPLE 5

(2R, 10S)-10-(4-Fluorophenyl)-10-hydroxy-2-methyl-2,10-dihydroimidazo[1,2-b]isoquinolin-5(3H)-one A mixture of 1-(4-fluorophenyl)-3-oxo-1,3-dihydro-2-benzofuran-1-carboxamide (12.5 g) (Step 1 of Example 2), 1,2-diaminopropane (13.5 g), and toluene (150 mL) was heated at reflux for 18 h in a flask equipped with a water separator. The mixture was evaporated to dryness. The residue was treated with hot ethanol (200 mL). The insoluble material was collected by filtration and dried to give the title compound (4.3 g) as a white solid m.p. 229–232° C. Mass spectrum (EI, M$^+$) m/z 310. $^1$H NMR (400 MHz, DMSO-d$_6$) δ 8.04 (d, 1H), 7.62 (t, 1H), 7.51 (t, 1H), 7.33 (m, 3H), 7.10 (t, 2H), 7.04 (s, 1H), 4.13 (m, 1H), 4.02 (dd, 1H), 3.52 (dd, 1H), and 1.20 ppm (d, 3H).

Anal. for $C_{18}H_{15}N_2O_2F$: Calculated: C, 69.67; H, 4.87; N, 9.03. Found: C, 69.86; H, 4.77; N, 9.14.

EXAMPLE 6

(2S,10S)-10-(4-Fluorophenyl)-10-hydroxy-2-methyl-2,10-dihydrolmidazo[1,2-b]isoquinolin-5(3H)-one The ethanolic filtrate that was obtained from the procedure described in Example 5 was evaporated to dryness. The residue was purified by flash chromatography on silica gel using methanol/methylene chloride (8:92). Crystallization from ethyl acetate/hexane afforded the title compound (2.9 g) as a white solid m.p. 142–146° C. Mass spectrum (EI, M$^+$) m/z 310. $^1$H NMR (400 MHz, DMSO-d$_6$) δ 8.03 (d, 1H), 7.61 (t, 1H), 7.49 (t, 1H), 7.39 (d, 1H), 7.33 (m, 2H), 7.09 (t, 2H), 6.96 (s, 1H), 4.20 (m, 1H), 4.14 (dd, 1H), 3.45 (dd, 1H), and 1.13 ppm (d, 3H).

Anal. for $C_{18}H_{15}N_2O_2F$. Calculated: C, 69.67; H, 4.87; N, 9.03. Found: C, 69.44; H, 4.84; N, 9.19.

EXAMPLE 7

10-(4-Chlorophenyl)-10-hydroxy-2,2-dimethyl-2,10-dihydroimidazo[2,1-g][1,7]naphthyridin-5(3H)-one A mixture of 3-(4-chlorobenzoyl)-2-pyridinecarboxylic acid (13 g), potassium cyanide (4.56 g), and acetic acid (30 mL) was heated at 120–125 C. in a sealed pressure bottle for 48 h. After cooling to ambient temperature, the mixture was poured into ice water. The precipitated solid was dissolved in ethyl acetate, washed with sodium bicarbonate saturated solution then with water. The organic phase was dried over anhydrous magnesium sulfate and evaporated to dryness. The residue was treated with ether. The formed solid was collected by filtration and dried to give 10.2 g of 5-(4-chlorophenyl)-7-oxo-5,7-dihydrofuro[3,4-b]pyridine-5-carboxamide. A mixture of 5-(4-chlorophenyl)-7-oxo-5,7-dihydrofuro[3,4-b]pyridine-5-carboxamide (5 g), 2-methyl-1,2-diamino propane (6.3 g), and toluene (80 mL) was heated at reflux for 18 h in a flask equipped with a water separator. The mixture was cooled to ambient temperature. The precipitated material was collected by filtration and dried to give the title compound (2.4 g), m.p. 257–260° C.

Anal. for $C_{18}H_{16}N_3O_2Cl$ Calculated: C, 63.25; H, 4.72; N, 12.29. Found: C, 63.21; H, 4.64; N, 12.26.

In a similar manner, using the appropriate starting materials, the following compounds were prepared:

EXAMPLE 8

11-(4-Chlorophenyl)-11-hydroxy-2,3,4,11-tetrahydro-6H-pyrimido[1,2-b]isoquinolin-6-one
m.p. 128–130° C.

Anal. for $C_{18}H_{15}N_2O_2Cl$ Calculated: C, 66.15; H, 4.62; N, 8.57; Cl, 9.80. Found: C, 66.20; H, 4.59; N, 8.59; Cl, 9.6 m.p. 139–141° C. Anal. for $C_{18}H_{16}N_2O_2$ Calculated: C, 73.95; H, 5.51; N, 9.58. Found: C, 73.66; H, 5.42; N, 9.50.

EXAMPLE 10

10-(4-Chlorophenyl)-10-hydroxy-2,2-dimethyl-2,10-dihydroimidazo[1,2-b]isoquinolin-5(3H)-one m.p. 181–183° C. Anal. for $C_{19}H_{17}N_2O_2Cl$ Calculated: C, 66.96; H, 5.03; N, 8.22; Cl, 10.41. Found: C, 66.80; H, 5.08; N, 8.14; Cl, 10.79.

EXAMPLE 11

10-(4-Chlorophenyl)-10-hydroxy-2,10-dihydroimidazo[1,2-b]isoquinolin-5(3H)-one m.p. 235–237° C. Anal. for $C_{17}H13N_2O_2Cl$ Calculated: C, 65.30; H, 4.19; N, 8.96; Cl, 11.34. Found: C, 65.22; H, 4.18; N, 8.87; Cl, 11.21.

EXAMPLE 12

10-Hydroxy-10-phenyl-2,10-dihydroimidazo[1,2-b]isoquinolin-5(3H)-one m.p. 263–265° C. Anal. for $C_{17}H_{14}N_2O_2$ Calculated: C, 73.46; H, 5.07; N, 10.07. Found: C, 73.28; H, 5.15; N, 9.98.

EXAMPLE 13

10-(4-Bromophenyl)-10-hydroxy-2,10-dihydroimidazo[1,2-b]isoquinolin-5(3H)-one m.p. 212–215° C. Anal. for $C_{17}H_{13}N_2O_2Br$ Calculated: C, 57.16; H, 3.67; N, 7.84. Found: C, 57.39; H, 3.87; N, 7.96.

The present invention may be embodied in other specific forms without departing from the spirit and essential attributes thereof and accordingly, reference should be made to the appended claims, rather than to the foregoing specification, as indicating the scope of the invention.

What is claimed is:

1. An antiatherosclerotic compound of the formula:

(I)

wherein:

R is hydrogen, lower alkyl, alkenyl, alkynyl, aryl, heteroaryl, or aryl or heteroaryl substituted with one or more members of the group consisting of alkyl, hydroxy, alkoxy, perfluoroalkyl, perfluoroalkoxy, alkylthio, nitro, amino, mono or di-alkylamino, and halogen;

D is C—H, carbon bound to $R_5$ or nitrogen;

$R_1$, $R_2$, $R_3$, and $R_4$ are each independently hydrogen, alkyl, or taken together form a ring;

$R_5$ is one or more groups selected from hydrogen, alkyl, alkenyl, alkynyl, aryl, hydroxy, alkoxy, perfluoroalkyl, perfluoroalkoxy, alkylthio, nitro, amino, mono or di-alkylamino, or halogen;

n is an integer of 0–3;

or a pharmaceutically acceptable salts thereof.

2. The antiatherosclerotic compound of claim 1 wherein,

R is aryl;

D is C—H;

$R_1$, $R_2$, $R_3$, and $R_4$ are each independently hydrogen, alkyl or taken together form a ring;

$R_5$ is halogen;

n is 0 or 1;

or a pharmaceutically acceptable salts thereof.

3. The antiatherosclerotic compound of claim 1 which is 10-Hydroxy-2,2-dimethyl-10-phenyl-2,10-dihydroimidazo[1,2-b]isoquinolin-5(3H)-one;

4. The antiatherosclerotic compound of claim 1 which is 11-(4-Fluorophenyl)-11-hydroxy-2,3,4,11-tetrahydro-6H-pyrimido[1,2-b]isoquinolin-6-one.

5. The antiatherosclerotic compound of claim 1 which is 10-(4-Fluorophenyl)-10-hydroxy-2,2-dimethyl-2,10-dihydroimidazo[1,2-b]isoquinolin-5(3H)-one.

6. The antiatherosclerotic compound of claim 1 which is 6-(4-Fluorophenyl)-6-hydroxy-1,3,4,4a,6,12a-hexahydrobenzimidazo[1,2-b]isoquinolin-11(2H)-one.

7. The antiatherosclerotic compound of claim 1 which is (2R,10S)-10-(4-Fluorophenyl)-10-hydroxy-2-methyl-2,10-dihydroimidazo[1,2-b]isoquinolin-5(3H)-one.

8. The antiatherosclerotic compound of claim 1 which is (2S,10S)-10-(4-Fluorophenyl)-10-hydroxy-2-methyl-2,10-dihydroimidazo[1,2-b]isoquinolin-5(3H)-one.

9. The antiatherosclerotic compound of claim 1 which is 10-(4-Chlorophenyl)-10-hydroxy-2,2-dimethyl-2,10-dihydroimidazo[2,1-g][1,7]naphthyridin-5(3H)-one.

10. A pharmaceutical composition which comprises an anti-atherosclerotic compound of the formula:

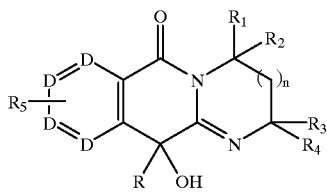

(I)

wherein:

R is hydrogen, lower alkyl, alkenyl, alkynyl, aryl, heteroaryl, or aryl or heteroaryl substituted with one or more members of the group consisting of alkyl, hydroxy, alkoxy, perfluoroalkyl, perfluoroalkoxy, alkylthio, nitro, amino, mono or di-alkylamino, and halogen;

D is C—H, carbon bound to $R_5$ or nitrogen;

$R_1$, $R_2$, $R_3$, and $R_4$ are each independently hydrogen, alkyl, or taken together form a ring;

$R_5$ is one or more groups selected from hydrogen, alkyl, alkenyl, alkynyl, aryl, hydroxy, alkoxy, perfluoroalkyl, perfluoroalkoxy, alkylthio, nitro, amino, mono or di-alkylamino, or halogen;

n is an integer of 0–3;

or a pharmaceutically acceptable salt thereof.

11. A method of treating atherosclerosis in a patient in need thereof, which comprises administering to said patient an anti-atherosclerotic effective amount of a compound of the formula:

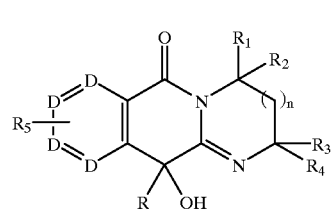

(I)

wherein:

R is hydrogen, lower alkyl, alkenyl, alkynyl, aryl, heteroaryl, or aryl or heteroaryl substituted with one or more members of the group consisting of alkyl, hydroxy, alkoxy, perfluoroalkyl, perfluoroalkoxy, alkylthio, nitro, amino, mono or di-alkylamino, and halogen;

D is C—H, carbon bound to $R_5$ or nitrogen;

$R_1$, $R_2$, $R_3$, and $R_4$ are each independently hydrogen, alkyl, or taken together form a ring;

$R_5$ is one or more groups selected from hydrogen, alkyl, alkenyl, alkynyl, aryl, hydroxy, alkoxy, perfluoroalkyl, perfluoroalkoxy, alkylthio, nitro, amino, mono or di-alkylamino, or halogen;

n is an integer of 0–3;

or a pharmaceutically acceptable salt thereof.

* * * * *